(12) United States Patent
Duineveld et al.

(10) Patent No.: US 12,569,297 B2
(45) Date of Patent: Mar. 10, 2026

---

(54) COOLING FOR A PERSONAL CARE DEVICE

(71) Applicant: KONINKLIJKE PHILIPS N.V.,
Eindhoven (NL)

(72) Inventors: Paulus Cornelis Duineveld, Drachten
(NL); **Timotheus Johannes Maria Van
Aken**, Emmen (NL)

(73) Assignee: KONINKLIJKE PHILIPS N.V.,
Eindhoven (NL)

( * ) Notice: Subject to any disclaimer, the term of this
patent is extended or adjusted under 35
U.S.C. 154(b) by 439 days.

(21) Appl. No.: 17/923,053

(22) PCT Filed: Jun. 4, 2021

(86) PCT No.: PCT/EP2021/065024
§ 371 (c)(1),
(2) Date: Nov. 3, 2022

(87) PCT Pub. No.: WO2021/245243
PCT Pub. Date: Dec. 9, 2021

(65) Prior Publication Data
US 2023/0149078 A1 May 18, 2023

(30) Foreign Application Priority Data
Jun. 5, 2020 (EP) .................................... 20178596

(51) Int. Cl.
*A61B 18/18* (2006.01)
*A61B 18/00* (2006.01)

(52) U.S. Cl.
CPC .... *A61B 18/18* (2013.01); *A61B 2018/00017*
(2013.01); *A61B 2018/00029* (2013.01);
(Continued)

(58) Field of Classification Search
CPC ...................................................... A61B 18/18
See application file for complete search history.

(56) References Cited

U.S. PATENT DOCUMENTS 6,187,001 B1 * 2/2001 Azar .................... A61B 18/203
606/9
6,214,034 B1 4/2001 Azar
(Continued)

FOREIGN PATENT DOCUMENTS

EP          1058569 B1   3/2003
JP       2009034234 A    2/2009
(Continued)

OTHER PUBLICATIONS

International Search report and Written Opinion of PCT/EP2021/
065024 dated Sep. 14, 2021.

*Primary Examiner* — Carl H Layno
*Assistant Examiner* — Bryan McAllister Lee

(57) ABSTRACT

A personal care device configured to perform an energy-
based treatment on a body of a subject, the personal care
device comprising: a main body portion including an energy
source and a cavity having a primary opening, the cavity
being configured to transmit treatment energy from the
energy source to the primary opening, wherein the primary
opening is configured to be placed against the body during
use of the device to define the portion of the body being
treated, and to define a volume of air within the cavity,
wherein the cavity comprises a secondary opening arranged
at a distance from the primary opening and at a distance
from the body when the primary opening is placed against
the body and configured to permit a flow of air via the
secondary opening and a flow of air out of the cavity into the
main body portion.

13 Claims, 10 Drawing Sheets

(52) U.S. Cl.
CPC ............... *A61B 2018/00476* (2013.01); *A61B 2018/0091* (2013.01); *A61B 2018/1807* (2013.01)

(56) References Cited

U.S. PATENT DOCUMENTS

| | | | |
|---|---|---|---|
| 2010/0063565 A1 | 3/2010 | Beerwerth | |
| 2010/0324544 A1 | 12/2010 | Fertner et al. | |
| 2011/0060322 A1* | 3/2011 | Manstein ............. | A61B 18/203 |
| | | | 606/9 |
| 2012/0010684 A1 | 1/2012 | Owens et al. | |

FOREIGN PATENT DOCUMENTS

| | | | |
|---|---|---|---|
| JP | 2012239780 A | 12/2012 | |
| KR | 20160146337 A | 12/2016 | |
| KR | 20170114628 A | 10/2017 | |
| WO | 9934867 A1 | 7/1999 | |
| WO | 9958195 A1 | 11/1999 | |
| WO | 2010032235 A1 | 3/2010 | |
| WO | 2014199365 A1 | 12/2014 | |
| WO | 2015098427 A1 | 7/2015 | |
| WO | 2018185773 A | 10/2018 | |

* cited by examiner

COOLING FOR A PERSONAL CARE DEVICE

CROSS-REFERENCE TO PRIOR APPLICATIONS

This application is the U.S. National Phase application under 35 U.S.C. § 371 of International Application No. PCT/EP2021/065024, filed on Jun. 4, 2021, which claims the benefit of European Patent Application No. 20178596.1, filed on Jun. 5, 2020. These applications are hereby incorporated by reference herein.

FIELD OF THE INVENTION

The present disclosure relates to personal care devices, and is particularly, although not exclusively, concerned with a skin care device configured to perform an energy-based treatment on a body of a subject.

BACKGROUND OF THE INVENTION

Many types of personal care device exist that can be used to perform an energy-based treatment on a subject, for example on the hair and/or skin of the subject.

Light-based hair removal is a treatment used to inhibit the growth of hair by exposing the skin to bright flashes or pulses of light, which can be referred to as IPL (Intense Pulsed Light) where the light pulse is generated by a lamp or light bulb. Alternatively the flash or pulse can be generated using a laser or one or more light emitting diodes (LEDs). The light penetrates the skin and is absorbed-among other places—in the root of the hair. The temperature of the root of the hair will rise and subsequently the temperature of the surrounding tissue will also rise. The growth of the hair is inhibited if the temperature rise is sufficient. This process is known as photothermolysis.

A personal care device may include one or more sensors for monitoring one or more parameters before or during a personal care operation. For example, contact with skin is required for successful photoepilation treatment and to prevent a light pulse being directed into other body parts such as eyes, which can result in injury. Therefore the personal care device may include a skin contact sensor for measuring or detecting contact with the skin. Another type of sensor used in personal care devices is a skin tone sensor that measures the tone of the skin to which an energy-based treatment (e.g. photoepilation) is to be applied.

Personal care devices performing an energy-based treatment may heat up during use, especially during prolonged periods of use. Increasingly stringent safety standards (e.g. IEC 60601) describe maximum temperature limits for parts of personal care devices having contact with the body of a subject.

To ensure compliance with such safety standards, a temperature sensor is often provided on a part of a personal care device having contact with the body of a subject. If the temperature of a part of the device rises above a temperature limit, the device may 'time-out' to allow cooling.

EP1058569 A1 (WO 99/34867) discloses a device which comprises a housing 32, the housing 32 comprising a flash lamp 14 and an air cavity 11. The air cavity has a primary opening which is placed against the body and directs the lamp energy to the hair. In FIG. 5A, the housing 32 further includes an opening which allows the air to be pumped out of the cavity via an air pump.

SUMMARY OF THE INVENTION

It is desirable that external components of a personal care device remain within temperature ranges that are comfortable for users. The present inventors have determined that the air contained within a personal care device's treatment cavity may be incidentally heated by the treatment energy as it passes through the treatment cavity, causing a rise in temperature and pressure of this confined air. The heated air may leave from the treatment cavity via the opening in contact with the body of the subject, the heated air thus passing across the body of the subject and heating up external surfaces of the device. This may negatively affect user experience. Improved cooling arrangements may thus be desirable. Further, it would be advantageous to perform cooling whilst the device is performing the energy-based treatment.

According to a first specific aspect, there is provided a personal care device configured to perform an energy-based treatment on a portion of a body of a subject, the personal care device comprising: an energy source; and a cavity having a primary opening, the cavity being configured to transmit treatment energy from the energy source to the primary opening, wherein the primary opening is configured to be placed against the body during use of the personal care device to define the portion of the body being treated by means of the treatment energy, and to define a volume of air within the cavity, wherein the cavity comprises a secondary opening arranged at a distance from the primary opening and at a distance from the body when the primary opening is placed against the body and configured to permit a flow of air via the secondary opening and, thereby, a flow of air out of the cavity whilst treatment energy is transmitted from the energy source to the primary opening.

The secondary opening may be configured to permit a flow of air via the secondary opening into the cavity and via the primary opening out of the cavity. The secondary opening may be configured such that, during use, the cavity is in fluidic communication with an internal air flow within the personal care device via the secondary opening. The secondary opening may be configured to be permanently open. The secondary opening may be provided along an axis tilting away from a direction of propagation of treatment energy generated by the energy source. The secondary opening may be provided along an axis tilting away from a direction of propagation of treatment energy incident upon the secondary opening during use. The secondary opening may be provided along an axis passing through the primary opening of the cavity. The secondary opening may be provided along an axis configured to restrict a loss of treatment energy, generated by the energy source, from the cavity via the secondary opening.

The cavity may comprise at least one reflector wall configured to reflect and thereby direct treatment energy from the energy source towards the primary opening of the cavity. The secondary opening may be provided in the reflector wall. The cavity may comprise a plurality of secondary openings.

The secondary opening may comprise a leading edge and a trailing edge, the leading edge being configured to extend beyond the trailing edge with respect to a direction of propagation of treatment energy incident upon the secondary opening, the secondary opening thereby being configured to restrict a loss of treatment energy from the cavity via the secondary opening.

The personal care device may comprise an auxiliary reflector provided externally of the cavity and in alignment with the secondary opening, the auxiliary reflector being configured to reflect treatment energy propagating from the cavity into the secondary opening back into the cavity via the secondary opening. The personal care device may comprise a reflective surface provided within the secondary opening, the reflective surface being configured to restrict a loss of treatment energy from the cavity via the secondary opening.

The personal care device may further comprise a supporting surface surrounding the primary opening and arranged to contact and support the portion of the body during use. The supporting surface may comprise at least one groove configured to be in fluidic communication with the cavity and with ambient air when the supporting surface is in contact with the portion of the body. At least one protrusion may be provided on the supporting surface.

The personal care device may be a skin care device. The energy source may comprise a light source. The treatment energy may comprise intense pulsed light. The personal care device may comprise a detachable portion configured to be detachable from a main body portion of the personal care device, the detachable portion comprising the cavity, the primary opening and the secondary opening. The main body portion may comprise the energy source.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which.

DETAILED DESCRIPTION OF THE EMBODIMENTS

Figure 1:
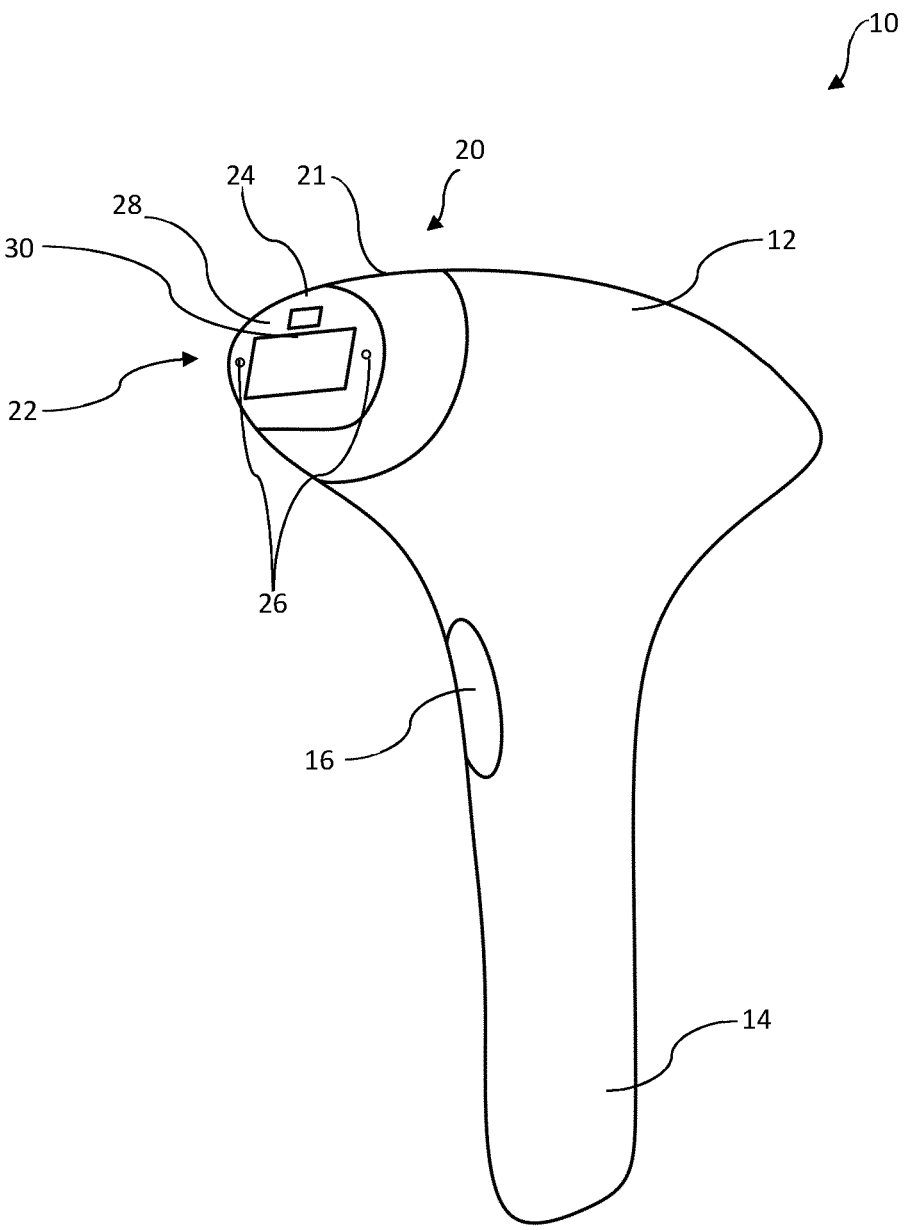
FIG. 1 is a perspective view of a personal care device.

With reference to FIG. 1, a personal care device 10 is configured to perform an energy-based treatment on a portion of a body of a subject. In particular, the personal care device 10 depicted in FIG. 1 is a skin care device configured to perform an intense pulsed light (IPL)-based treatment on a portion of a body of a subject, for the purposes of hair removal and/or hair growth inhibition, i.e. a photoepilator configured to perform photoepilation. However, it should be understood that the personal care device 10 depicted in FIG. 1 is merely presented as an example of a personal care device 10 to which the present invention may be applied. For example, the personal care device 10 may be configured to perform an alternative energy-based treatment, relating to heat, and/or light and/or to apply another form of treatment energy to the body, such as a dermatological treatment, including hair growth reduction, treating acne, a phototherapy treatment, skin rejuvenation, skin tightening, portwine stain treatment; and pain relief.

As described herein, the term 'user' refers to the person controlling the device, and the term 'subject' refers to the recipient of the treatment (e.g. a person or an animal). The user of the personal care device 10 may be the subject, or alternatively the personal care device 10 may be used by a user on a subject wherein the user and the subject are not the same.

The personal care device 10 comprises a main body portion 12 having a handle 14 and a user control 16. The handle 14 is shaped and sized such that the personal care device 10 can be grasped in one or both hands of a user. The user control 16 can be operated by the user (e.g. a user's digit from a hand grasping the handle 14) to activate the personal care device 10 so that the energy-based treatment is performed on the body of the subject. The user control 16 may be in the form of a switch, a button, a touch pad, etc.

The personal care device 10 comprises a detachable portion 20 configured to be detachable from, and re-attachable to, the main body portion 12. As will be described below, the detachable portion 20 is configured to interact and communicate with features of the main body portion 12.

For ease of reference, components of the personal care device 10 may be described in relation to the orientation shown in FIG. 1—the end of the personal care device 10, including the detachable portion 20, nearest the left hand side of the page, will be described as the 'front'; the end nearest the right hand side of the page will be described as the 'back'; the part of the device 10 nearest the top of the page as the 'top'; the end nearest the bottom of the page as the 'bottom'; the side of the device 10 into the page as 'left'; and the side of the device coming out of the page as 'right'. The top, bottom, left and right directions may be indicated in reference numerals with the letters 'T', 'B', 'L' and 'R' respectively.

Figure 2:
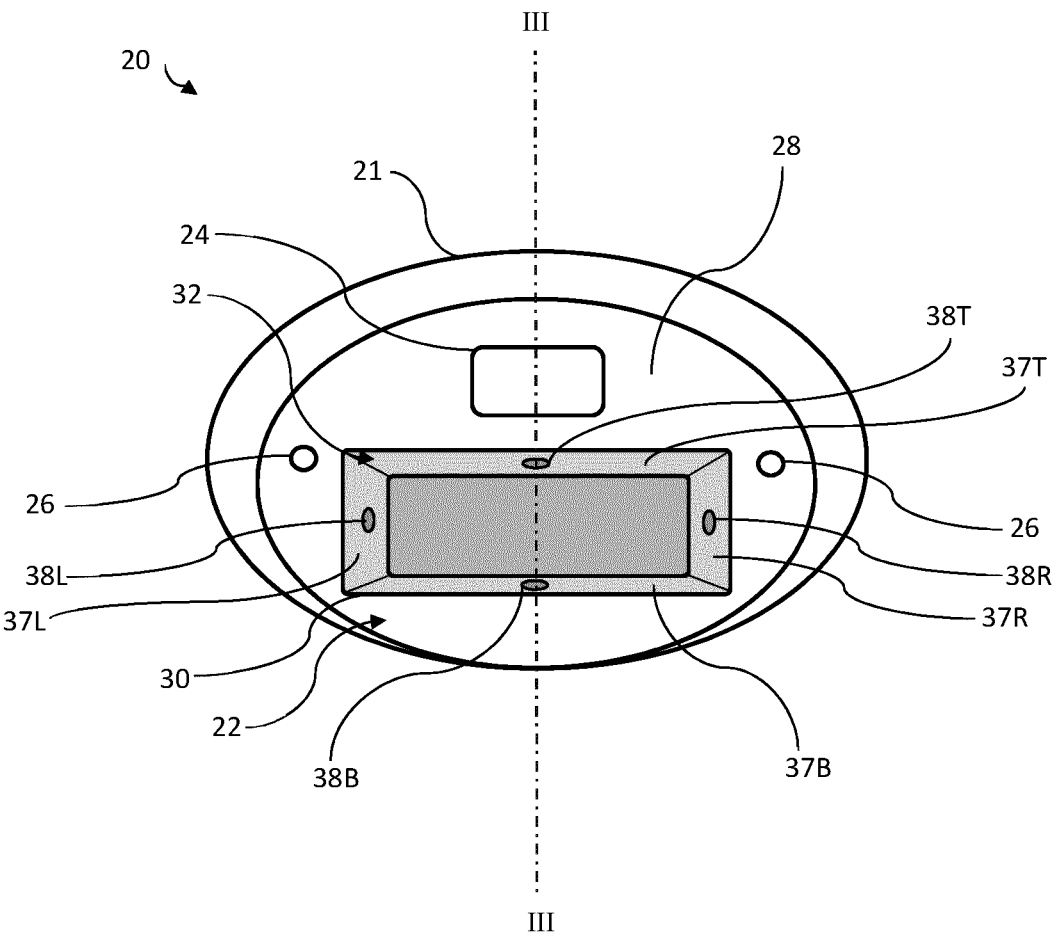
FIG. 2 is a front view of a detachable portion of the personal care device

FIG. 2 shows a front view of the detachable portion 20 of the personal care device 10. A schematic representation of a vertical section through the detachable portion 20 along the line III-III is shown in FIG. 3.

Figure 3:
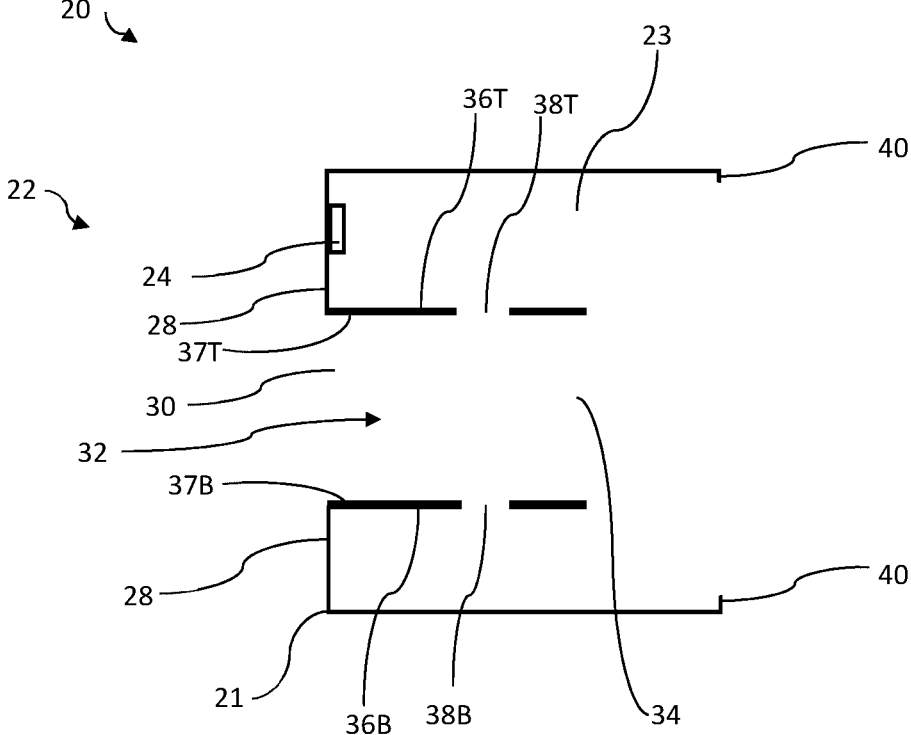
FIG. 3 is a schematic section through the detachable portion of FIG. 2 along the line III-III.

With reference to FIG. 1, FIG. 2 and FIG. 3, the detachable portion 20 comprises a housing 21 having a face 22 which is configured to be placed, in use, against a body of a subject. The face 22 comprises a skin tone sensor 24 which may be used to determine the skin tone of the portion of the body on which the personal care device 10 is used, such that a suitable dose of energy-based treatment may be administered to the portion of the body of the subject. The face 22 additionally comprises two skin contact sensors 26, which may be provided on or in the face 22, and configured to determine whether the face 22 is in contact with the body of the subject. The skin contact sensors 26 may measure a parameter that is indicative of whether the face 22 is in contact with skin, and generate respective measurement signals (referred to as 'skin contact measurement signals'). Typically a skin contact sensor 26 is used in a personal care device 10, particularly a photoepilator, to make sure that the personal care device 10 is correctly in contact with skin before a light pulse is generated to avoid the light pulse being directed into the eyes of the user or subject.

The parameter can be capacitance, and so the skin contact sensors 26 can measure capacitance via a respective pair of electrical contacts or electrodes on the surface of the face 22, with the measured capacitance being indicative of whether there is skin contact. Alternatively, the parameter can be an intensity or level of light, and so the skin contact sensors 26 can be light sensors that measure an intensity or level of light incident on the light sensor, with the measured intensity or level being indicative of whether there is skin contact (e.g.

less/no light could indicate skin contact as the skin obscures the light sensors 26, and vice versa). In other alternatives, the parameter can be a measure of contact pressure, and so the skin contact sensors 26 can measure contact pressure via respective pressure sensors or mechanical switches, with the measured contact pressure being indicative of whether there is skin contact.

The detachable portion 20 comprises an engagement portion 40, which may, for example, comprise barbed flanges or tabs, configured to engage a corresponding portion (not shown) of the main body portion 12. Detachment of the detachable portion 20 from the main body portion 12 may require a threshold force in order to disengage the corresponding engagement portions 40.

The face 22 comprises a primary opening 30 formed where a cavity 32 of the detachable portion 20 intersects the face 22. A supporting surface 28 is provided about the primary opening 30, the supporting surface 28 being configured, in use, to be placed against the body of the subject being treated.

Figure 5:
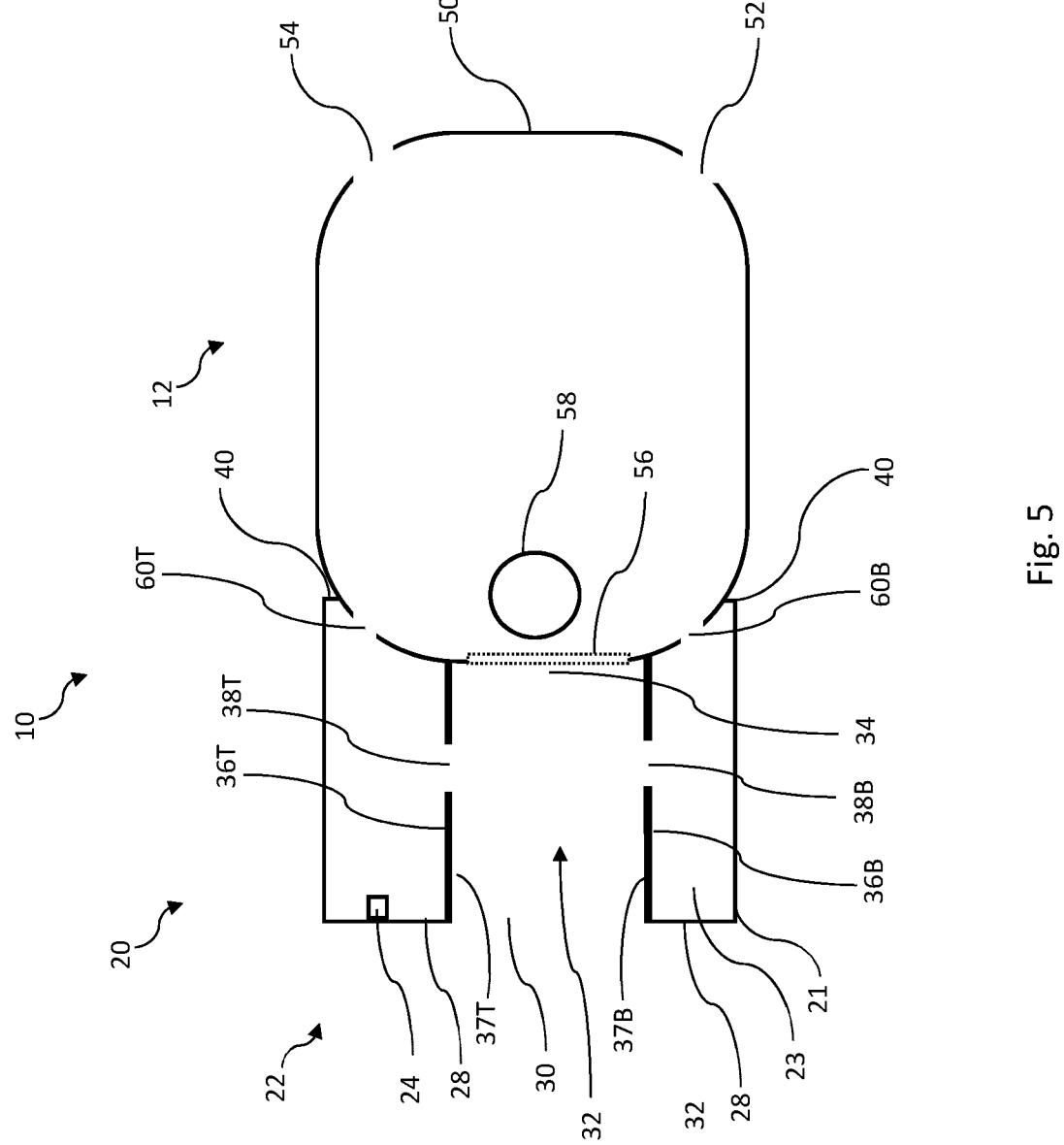
FIG. 5 is a schematic section through the personal care device when the detachable portion is attached to the main body portion

The cavity 32 is configured to transmit energy from an energy source 58 (FIG. 5) to the primary opening 30. For example, an energy source 58 may be provided outside of the cavity 32 and treatment energy may be transmitted into the cavity, e.g. by an energy window 56 (FIG. 5). A reflector (not shown) may be provided about the energy source 58 to direct treatment energy into the cavity 32. The cavity 32 may be configured to transmit treatment energy from an internal end 34 of the cavity 32 towards the primary opening 30. Additionally or alternatively, an energy source 58 may be provided within the cavity 32, and the cavity 32 may be configured to transmit treatment energy from an energy source 58 disposed part way along, i.e. within, the cavity 32, towards the primary opening 30.

The cavity 32 comprises at least one reflector wall 36T, 36B, 36L, 36R (collectively 36) configured to reflect, and thereby direct, treatment energy towards the primary opening 30. The at least one reflector wall 36 is opaque to the treatment energy emitted by the energy source 58. In the example shown in FIG. 2 and FIG. 3, the top, bottom, left and right reflector walls 36T, 36B, 36L, 36R each comprise a respective reflective surface 37T, 37B, 37L, 37R (collectively 37) within the cavity 32. It will be understood by the skilled person that alternative reflector wall 36 configurations may be suitable, for example a reflector wall of circular cross section rather than rectangular. Additionally or alternatively, not every reflector wall 36 may require or comprise a reflective surface 37.

A secondary opening 38T, 38B, 38L, 38R (collectively 38) is provided in at least one of the reflectors walls 36. In the example shown in FIG. 2 and FIG. 3, a respective secondary opening 38T, 38B, 38L, 38R is provided in each of the top, bottom, left and right reflector walls 36T, 36B, 36L, 36R. The secondary opening 38 is arranged at a distance from the primary opening 30, such that in use, the secondary opening 38 is provided at a distance from the body of the subject. The secondary opening 38 is configured to permit a flow of air via the secondary opening 38 and, thereby, a flow of air out of the cavity 32 whilst treatment energy is transmitted from the energy source 58 to the primary opening 30. The secondary opening 38 may be configured to be permanently open. For example, the secondary opening 38 may be configured to permit a flow of air, via the secondary opening 38, into the cavity 32 and, via the primary opening 30, out of the cavity 32, whilst treatment energy is transmitted from the energy source 58 to the primary opening 30. The secondary opening 38 may be configured to permit a flow of air into and/or out of the cavity whilst treatment energy is not being transmitted from the energy source 58 to the primary opening 30 (e.g. immediately after the transmission of treatment energy).

Each secondary opening 38 may comprise a cross section of any suitable shape, including but not limited to a circle, an ellipse, a square, a rectangle, or an annulus. In the example shown in FIG. 2 and FIG. 3, each secondary opening 38 has a circular cross section.

Figure 4:
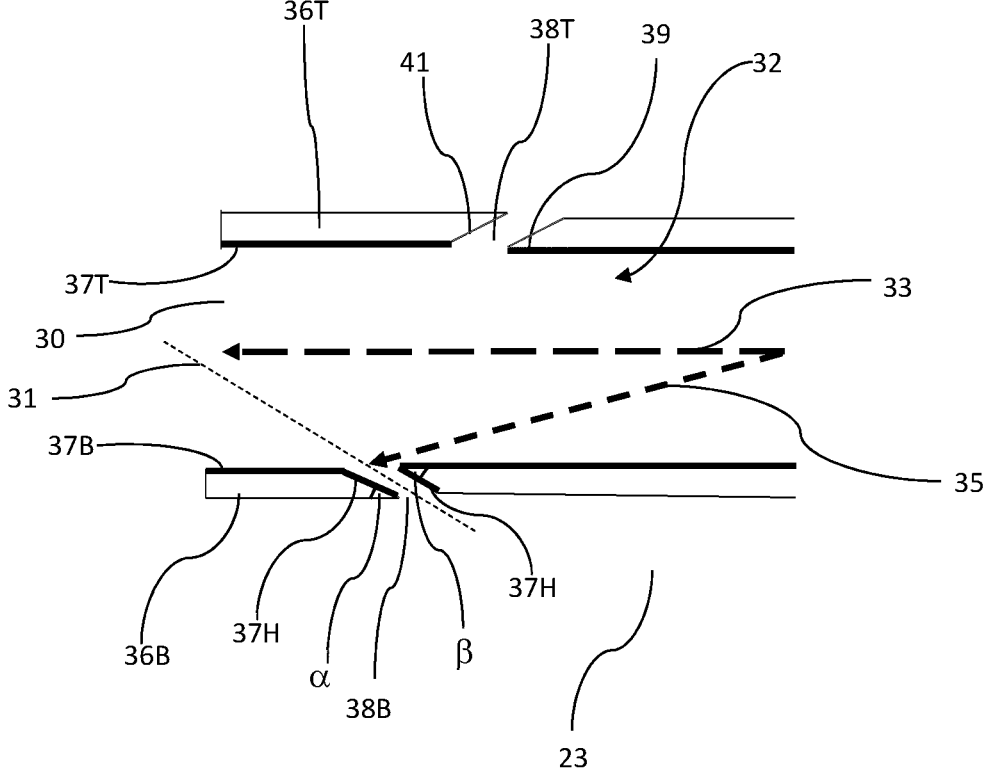
FIG. 4 is a schematic section through the cavity of the personal care device.

The secondary opening 38 may be configured to restrict a loss of treatment energy from the cavity 32 via the secondary opening 38 (e.g. for a photoepilator, to minimise a loss in optical efficiency). FIG. 4 shows a schematic section through a cavity 32 comprising a secondary opening 38 configured to restrict a loss of treatment energy via secondary opening 38. The secondary opening 38 shown in FIG. 4 is provided along an axis 31 which is offset or tilted away from a direction of propagation 33 of treatment energy, and offset or tilted away from a direction 35 of treatment energy incident upon the secondary opening 38B. Additionally or alternatively, the secondary opening 38 may be provided along an axis 31 tilting away from a longitudinal axis of the cavity 32; and/or provided along an axis 31 passing through the primary opening 30 (e.g. a centre point of the primary opening 30).

The illustrated axis 31 of the secondary opening 38 gives rise, with respect to a direction of propagation 33 of treatment energy being incident upon the secondary opening 38, to a leading edge 39 of the reflector wall 36 and a trailing edge 41 of the reflector wall 36. The leading edge 39 may overlap and/or extend beyond the trailing edge 41 with respect to a direction of propagation 33 of treatment energy within the cavity 32. The leading edge 39 may be at an angle $\beta$ to the reflective surface 37B of the reflector wall 36B. The trailing edge 41 may be at an angle $\alpha$ to an external surface of the reflector wall 36B. Angle $\alpha$ may be less than or equal to angle $\beta$. Angle $\alpha$ may be less than 60°, preferably less than 45°. The difference between angle $\alpha$ and angle $\beta$ may be less than 90°.

Additionally or alternatively, the secondary opening 38 may be provided along an axis 31 which is perpendicular to a direction of propagation 33 of treatment energy towards the primary opening 30. The secondary opening 38 may be provided along an axis 31 which is perpendicular to a longitudinal axis of the cavity 32.

The secondary opening 38 may comprise a reflective surface 37H provided on an interior surface of the secondary opening 38, the reflective surface 37H being configured to restrict a loss of treatment energy from the cavity 32 via the secondary opening 38.

The secondary opening 38 may be configured to restrict a loss of treatment energy from the cavity 32 by limiting the cross sectional area (or, if a plurality of secondary openings 38, the total cross sectional area of the secondary openings 38). For example, if the treatment energy comprises light, then a reduced diameter of the secondary opening 38 will reduce optical losses from the cavity.

It would be advantageous if the cross sectional area of the secondary opening 38 (or, if a plurality of secondary openings 38, the total cross sectional area of the secondary openings 38) were large enough to allow sufficient air flow, and thus sufficient cooling, of the cavity 32 (e.g. sufficient cooling for the cavity 32 to remain below certain threshold temperatures). Preferably, the total area of the secondary openings 38 is more than 0.1 mm², more preferably more than 1 mm², most preferably 10 mm².

It would be advantageous if the hydraulic diameter of the secondary opening 38 (or, if a plurality of secondary openings 38, the total hydraulic diameter of the secondary openings 38) were small enough to reduce drag of air passing through the secondary openings 38 to negligible levels. The hydraulic diameter of each secondary opening 38 is preferably less than 10 mm, more preferably less than 0.5 mm. Accordingly, multiple secondary openings 38 may be required to meet both the area requirement and hydraulic diameter requirement.

The secondary openings 38 may be evenly and/or uniformly distributed throughout the reflector walls 36. In the example shown in FIG. 2 and FIG. 3, one secondary opening 38 is provided in the centre of each reflector wall 36. In alternative arrangements (not shown), multiple secondary openings 38 may be provided in each reflector wall 36 and/or at least one reflector wall 36 may comprise no secondary openings 38.

The skilled person will be able to determine the appropriate number of secondary openings 38 according to the parameters of the personal care device 10, including the rate of heat generation, and a balancing of the competing factors of cross sectional area, hydraulic diameter and energy loss from the cavity 32.

In one example not shown, the reflector wall 36 may comprise a plurality of louvres or slats arranged in parallel, having secondary openings 38 in the form of slits provided therebetween. A reflective surface 37 provided on each louvre may direct treatment energy towards the primary opening 30, whilst the slits therebetween permit a flow of air through the secondary openings 38. A leading edge 39 and trailing edge 41 configuration may then be achieved in a similar manner to FIG. 4.

FIG. 5 shows a schematic vertical section through the personal care device 10 when the detachable portion 20 is attached to the main body portion 12 by means of the engagement portion 40 and corresponding portion (not shown) of the main body portion 12. For simplicity, the handle 14 and user control 16 of the main body portion 12 have been omitted from FIG. 5.

The main body portion 12 comprises a housing 50 having an inlet vent 52 which may be configured to permit a flow of air into the main body portion 12, for example as a result of a suction created by a fan (not shown) provided within the main body portion 12. An outlet vent 54 may be provided on an opposite side of the main body portion 12 to the inlet vent 52, such that the flow of air within the main body portion 12 may be directed through and/or past the components of the main body portion 12, including an energy window 56 and an energy source 58, in order to perform cooling. It will be understood that additional components (not shown) may be present within the main body portion 12, for example components configured to direct the flow of air, and/or components towards which the flow of air may be directed for the purpose of cooling (e.g. a PCB).

The energy window 56 may be provided in the housing 50 at a front end of the main body portion 12, such that when the detachable portion 20 is attached to the main body portion 12, the internal end 34 of the cavity 32 may align with the energy window 56. Adjacent the energy window 56, an energy source 58 is provided within the main body portion 12. The energy source 58 may be any energy source 58 suitable for performing an energy-based treatment on the body of a subject. For example, in a skin care device configured to perform photoepilation, the energy source may comprise a lamp, LED, laser or other light source, configured to emit intense pulsed light of a required frequency.

The energy window 56 is configured to be substantially transparent to the treatment energy emitted by the energy source 58, and configured to transmit treatment energy from the energy source 58 provided inside the main body portion 12 to outside the main body portion 12. In particular, the energy window 56 is configured to transmit treatment energy from the energy source 58 into the cavity 32 of the detachable portion 20 in a direction having at least a component towards the primary opening 30.

The main body portion 12 further comprises at least one communication vent 60L, 60T (collectively, 60) configured to permit fluidic communication between the main body portion 12 and an internal space 23 of the detachable portion 20. In the example shown in FIG. 5, the main body portion 12 comprises two communication vents 60L, 60T at a front end of the housing 50 of main body portion 12, the communication vents 60L, 60T configured to ensure fluidic communication between the internal space 23 of the detachable portion 20 and the space within the housing 50 of the main body portion 12.

In effect, upon attachment of the detachable portion 20 to the main body portion 12, the primary opening 30 may be in (indirect) fluidic communication, via the internal space 23 of the detachable portion 20 and the communication vents 60 of the main body portion 12, with the inlet vent 52 and outlet vent 54 of the main body portion 12. A flow of air may thereby be permitted between the inlet vent 52 of the main body portion 12 and the primary opening 30 of the cavity 32.

In use, the detachable portion 20 is attached to the main body portion 12. The face 22 of the personal care device 10 is placed against the body of the subject, the body of the subject defining a volume of air within the cavity 32, and the primary opening 30 defining the portion of the body of the subject being treated. The user may then trigger activation of the energy source 58 by means of the user control 16. If the skin contact sensors 26 determine that the face 22 is in contact with the body of the subject, then the energy source 58 is activated with a dose of treatment energy according to the skin tone of the subject as detected by the skin tone sensor 24. The energy window 56 transmits the treatment energy from the energy source 58, provided inside the main body portion 12, to the cavity 32, and the reflector walls 36 reflect, and thereby direct, the treatment energy towards the primary opening 30 of the personal care device 10. Administering the treatment energy to the body of the subject performs the energy-based treatment on the portion of the body of the subject defined by the primary opening 30. The energy source 58 may be controlled by a controller to ensure a sufficient dose is administered, and/or to prevent an excessive dose being administered.

In placing the face 22 of the personal care device 10 against the body of the subject during use, an air flow into and/or out of the cavity 32 (e.g. via primary opening 30) may ordinarily be reduced. However, the secondary openings 38 of the present invention permit a flow of air out of the cavity 32, whilst the treatment energy is transmitted towards the primary opening 30. For example, air may be permitted to flow out of the cavity 32 via the primary opening 30 and/or any one or combination of the secondary openings 38T, 38B, 38L, 38R. Air may enter the cavity 32 via one or any combination of secondary openings 38. Air may enter the cavity 32 via primary opening 30. Air may leave the cavity 32 via one, or any combination of, the secondary openings 38. Air may leave the cavity 32 via primary opening 30.

It will be understood by the skilled person that a number of different air flow routes may be permitted by the arrangement of the primary opening 30, the secondary openings 38T, 38B, 38L, 38R, the communication vents 60L, 60T, the inlet vent 52 and the outlet vent 54. The nature and direction of each air flow route may depend, inter alia, upon the dimensions of each opening 30, 38 and vent 52, 54, 60, as well as the temperature reached within the cavity 32, relative pressures in different parts of the personal care device 10, the internal air flow rate of the main body portion 12, and the degree of reduction in air flow through the primary opening 30.

In one example air flow path, air may enter the main body portion 12 via inlet vent 52, and may pass clockwise with respect to FIG. 5. Air may enter detachable portion 20 via communication vent 60B. Air may enter into the cavity 32 via the secondary opening 38B. Air may leave the cavity 32 via primary opening 30. Air may leave the cavity 32 via secondary opening 38T.

In another example air flow path, air may enter the main body portion 12 via inlet vent 52, and may pass clockwise with respect to FIG. 5. Air may enter the detachable portion 20 via communication vent 60B. Air may enter cavity 32 via secondary opening 38B. Air may leave via secondary opening 38T, and may re-enter the main body portion 12 via communication vent 60T. Air may leave main body portion 12 via outlet vent 54. Air flow from secondary opening 38B to secondary opening 38T may draw air into the cavity 32 via primary opening 30, which may then leave cavity 32 via secondary opening 38T.

In a further example air flow path, air passing through the main body portion 12 from the inlet vent 52 to the outlet vent 54 may draw air into the main body portion 12 from the internal space of the detachable portion 20, which may in turn draw air into the internal space of the detachable portion 20 from the cavity 32 via secondary openings 38T, 38B, 38L, 38R, which may in turn draw air into the cavity 32 via primary opening 30. In effect, the air flow within the main body portion 12 may draw air into the cavity 32 via primary opening 30 as a result of fluidic communication between the cavity 32 and the main body portion 12.

It should be understood that the above example air flow paths are not necessarily exclusive. For example, each example air flow path may occur during a typical use cycle of the personal care device 10, in which the device 10 is placed against the body, the energy source 58 activated, then the personal care device 10 is moved away from the body, before being again placed against the body in a different location and the cycle repeated. In any case, the flow of air into and/or out of and/or through cavity 32 performs a cooling function in the cavity 32, such that air within the cavity 32 is cooled and/or such that the components of the cavity and adjoining the cavity 32, including the reflector walls 36, the face 22 and supporting surface 28, are cooled.

Figure 6A:
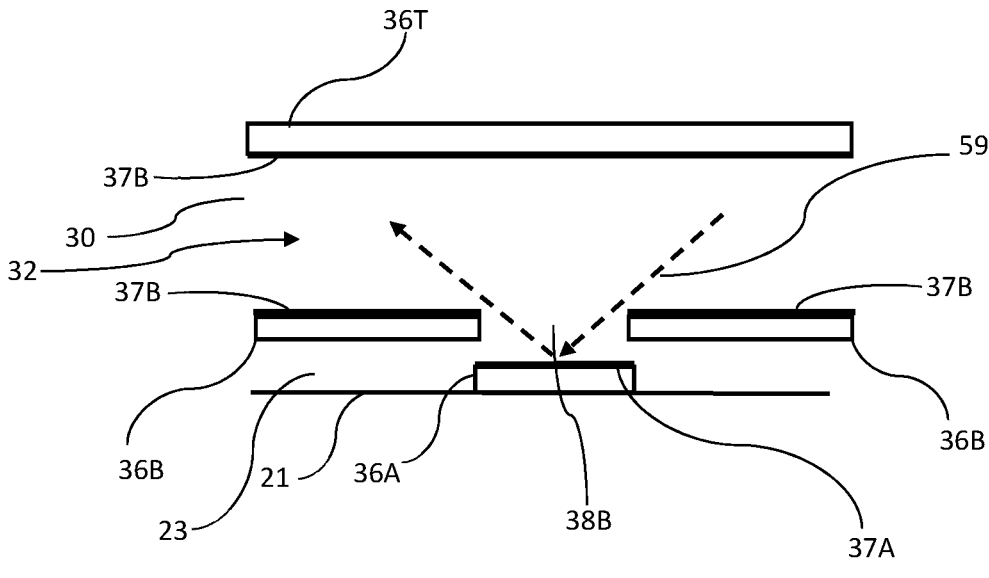
FIG. 6A, FIG. 6B and FIG. 6C show schematic sections through example reflector walls.
Figure 6B:
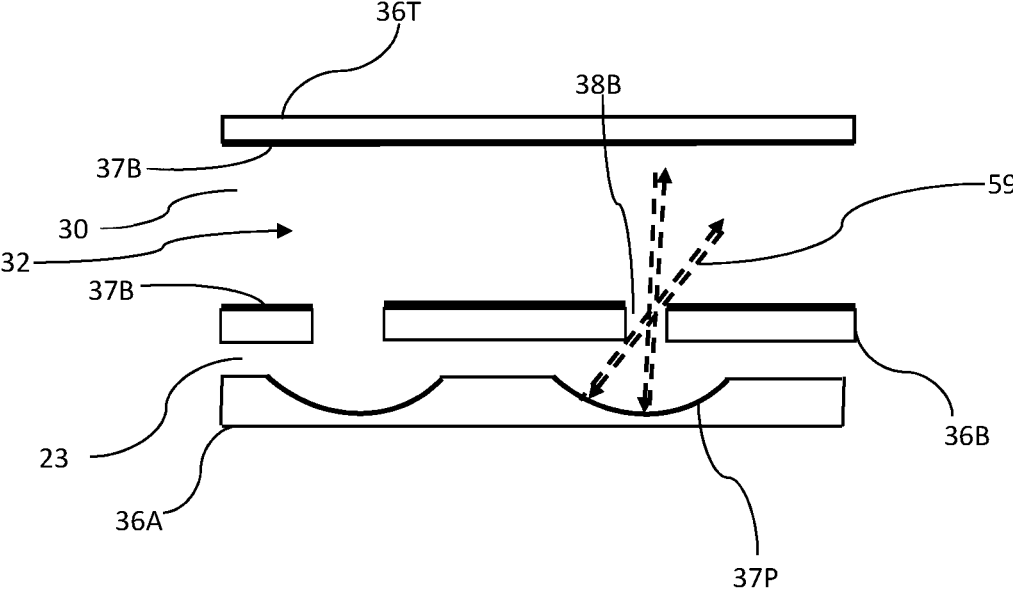
Figure 6C:
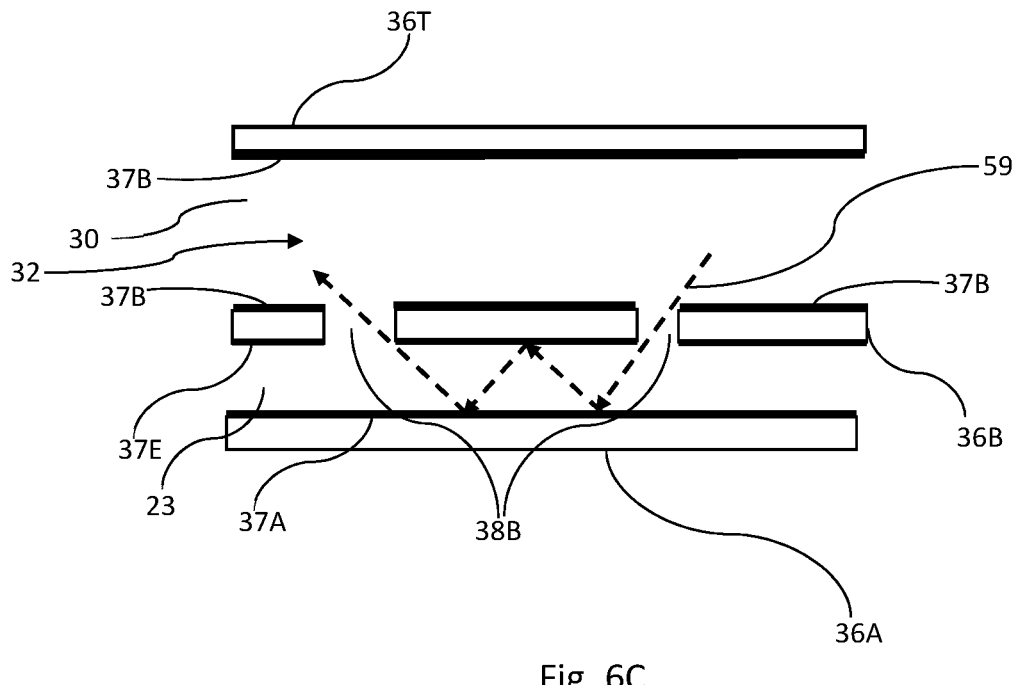

FIG. 6A, FIG. 6B and FIG. 6C, collectively FIG. 6, show a schematic section through a single reflector wall 36B of a cavity 32. An auxiliary reflector 36A may be provided externally to the cavity 32 and in alignment with the secondary opening 38 (e.g. in the internal space 23). The auxiliary reflector 36A may restrict and/or prevent a loss of treatment energy from the cavity 32 via the secondary opening 38. The auxiliary reflector 36A may be configured to reflect treatment energy propagating from the cavity 32 into the secondary opening 38 back into the cavity 32 via a secondary opening 38 (e.g. the same secondary opening 38 and/or a different secondary opening 38).

As shown in FIG. 6A, the auxiliary reflector 36A may comprise a reflective surface 37A (e.g. a planar reflective surface) substantially parallel to the reflector wall 36 of the cavity 32. The auxiliary reflector 36A may be configured (e.g. arranged sufficiently proximate to the secondary opening 38 and reflector wall 36) to reflect treatment energy propagating from the cavity 32 into the secondary opening 38B back into the cavity 32 via the same secondary opening 38B through which the energy left the cavity 32. The auxiliary reflector 36A may reflect the treatment energy 59 back into the cavity 32 in a direction having a component towards the primary opening 30, such that the treatment energy 59 may continue towards the body of the subject. The auxiliary reflector 36A may be disposed on or against the housing 21 of the detachable portion 20.

As shown in FIG. 6B, the auxiliary reflector 36A may comprise a parabolic reflective surface 37P, the auxiliary reflector 36A being configured to reflect treatment energy propagating from the cavity 32 into the secondary opening 38B back into the cavity 32 via the same secondary opening 38B through which the energy left the cavity 32. The parabolic reflective surface 37P may be configured such that its focus is located at a centre-point of the secondary opening 38B.

As shown in FIG. 6C, the auxiliary reflector 36A may comprise a planar reflective surface 37A disposed substantially parallel to the reflector wall 36 of the cavity 32, and running the length of the plurality of secondary openings 38 provided in the reflector wall 36. The reflector wall 36 may comprise a reflective surface 37E on its exterior, such that treatment energy may be reflected repeatedly between the reflective surface 37A of the auxiliary reflector 36A and the exterior reflective surface 37E of the reflector wall 36B. The auxiliary reflector may thereby be configured reflect treatment energy backing into the cavity 32 via a different secondary opening 38 from the secondary opening 38 through which the treatment energy left the cavity 32.

In an example not shown, the reflector wall 36 may comprise a one-way reflector, such that treatment energy being reflected from an auxiliary reflector 36A and incident upon an exterior surface of the reflector wall 36 may be transmitted into the cavity 32, but treatment energy incident upon the reflective surface 37 of the reflector wall 36 may be reflected so as to remain within the cavity 32. The secondary opening 38 may comprise a reflective surface 37 along its interior.

Figure 7:
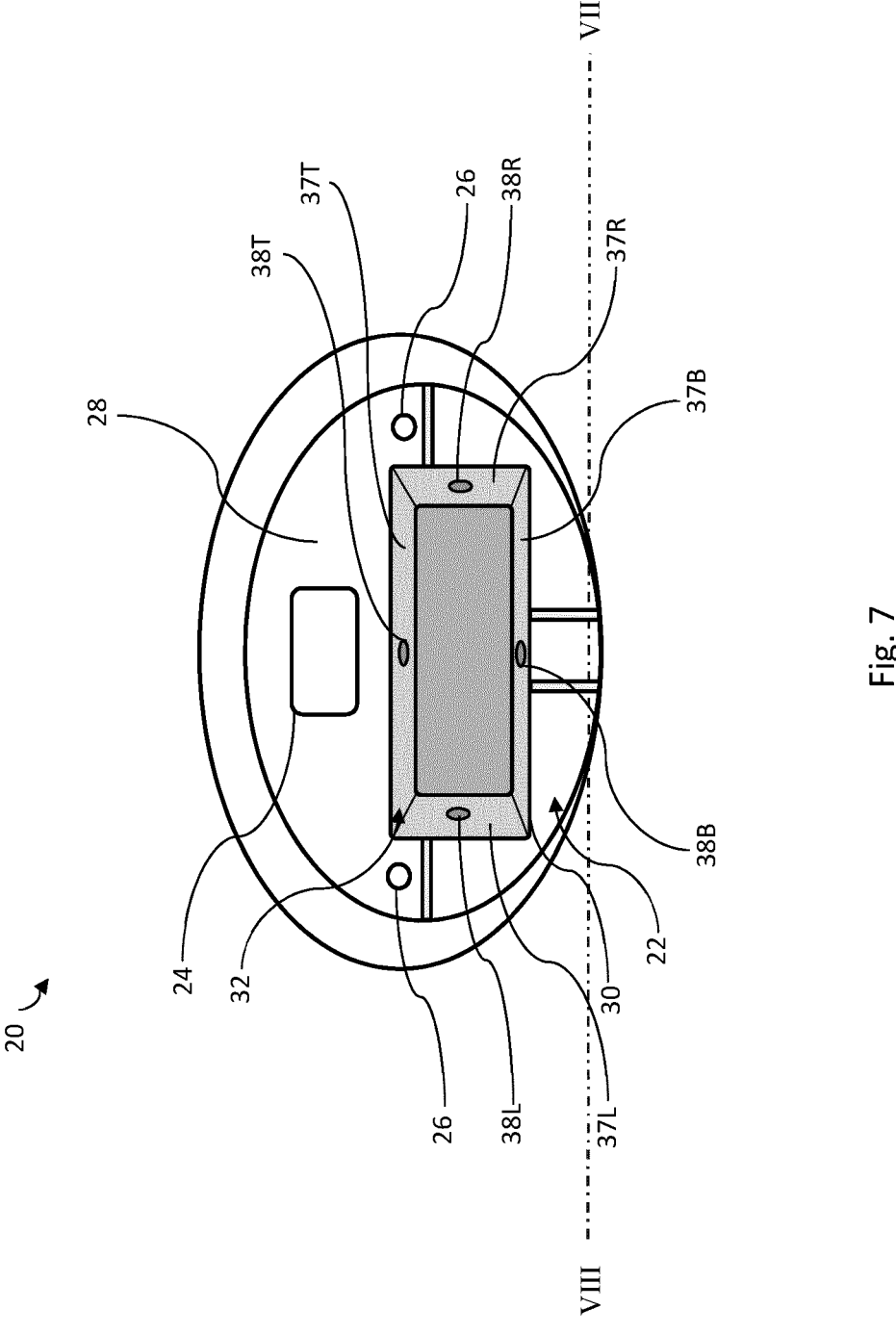
FIG. 7 is a front view of the detachable portion of the personal care device comprising surface features.

FIG. 7 shows a front view of the detachable portion 20 comprising at least one surface feature 64 and/or conduit 62 configured to permit fluidic communication between the cavity 32 and ambient air when the supporting surface 28 is in contact with the body of the subject. FIG. 8 shows a schematic section through the detachable portion of FIG. 7 along the line VIII-VIII.

With reference to FIG. 7 and FIG. 8, the supporting surface 28 may comprise at least one surface feature 64 and/or conduit 62 configured to permit fluidic communication between the cavity 32 and ambient air when the supporting surface 28 is in contact with the body 66 of the subject.

The surface feature 64 and/or conduit 62 may be of any suitable shape for permitting a flow of air through the primary opening 30. For example, the surface feature 64 and/or conduit 62 may be linear, or comprise a bend or kink along its length. The surface feature 64 and/or conduit 62 may be contiguous with the supporting surface 28.

Figure 8A:
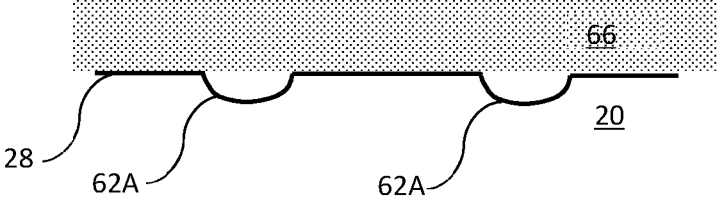
FIG. 8A to FIG. 8D show schematic sections through the line VIII-VIII of the detachable portion of FIG. 7.
Figure 8B:
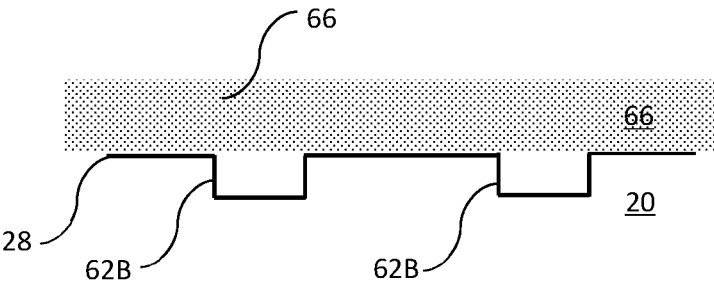

The surface feature 64 and/or conduit 62 may comprise a C-shaped groove 62A or channel as shown in FIG. 8A, or alternatively a straight-sided groove 62B or channel as shown in FIG. 8B.

Figure 8C:
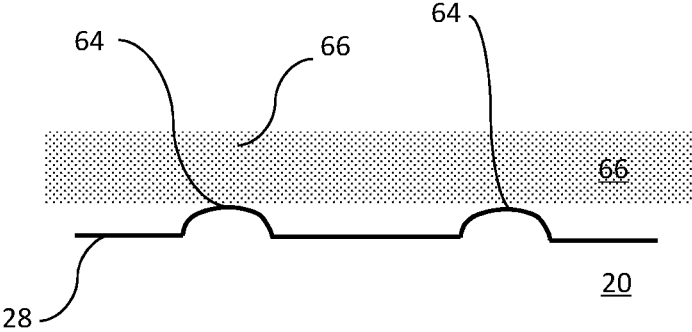

Additionally or alternatively, the surface feature 64 and/or conduit 62 may comprise at least one protrusion 64 (e.g. a plurality of bumps) as shown in FIG. 8C. The protrusion may be configured to ensure an imperfect contact between the supporting surface 28 and the body 66 of the user.

Figure 8D:
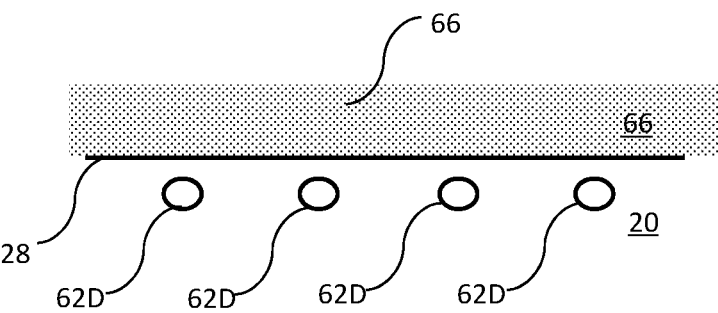

Additionally or alternatively further still, the surface feature 64 and/or conduit 62 may comprise at least one conduit 62D provided beneath the supporting surface 28, as shown in FIG. 8D.

One end of each conduit surface feature 64 and/or conduit 62 may terminate within the cavity 32, proximate to the primary opening 30. Another end of each conduit may terminate on an exterior surface of the housing 21 of the detachable portion 20, in communication with ambient air. In use, the supporting surface 28 is placed against the body 66 of the subject. The surface feature 64 and/or conduit 62 is configured to permit a flow of air through (e.g. into and/or out of) the primary opening 30 when the personal care device 10 is placed against the body 66 of the subject. In combination with the secondary openings 38, the groove may permit a flow of air into and/or out of (e.g. through) the cavity 32 during operation of the personal care device 10. For example, the groove may permit air entering the cavity 32 via the secondary opening 38 to exit the cavity 32 via the primary opening, whilst the personal care device is used and thus the supporting surface 28 is placed against the body/ skin of the subject.

Preferably, a width dimension of each surface feature 64 and/or conduit 62 may be between 0.1 mm and 20 mm, more preferably between 0.5 mm and 10 mm. Preferably, a height or depth of each surface feature 64 and/or conduit 62 may be greater than 0.1 mm, more preferably between 0.5 mm and 10 mm. Nevertheless, the skilled person will be able to determine the number, shape and dimensions of the surface feature 64 and/or conduit 62 according to the parameters of the personal care device 10 and the nature of the application.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A personal care device configured to perform an energy-based treatment on a portion of a body of a subject, the personal care device comprising:

a main body portion including an energy source; and a cavity having a primary opening, the cavity being configured to transmit treatment energy from the energy source to the primary opening, wherein the primary opening is configured to be placed against the body during use of the personal care device to define the portion of the body being treated by means of the treatment energy, and to define a volume of air within the cavity, wherein the cavity comprises a secondary opening arranged at a distance from the primary opening and at a distance from the body when the primary opening is placed against the body and configured to permit a flow of air via the secondary opening and, thereby, a flow of air out of the cavity into the main body portion whilst treatment energy is transmitted from the energy source to the primary opening, wherein the personal care device comprises a detachable portion configured to be detachable from the main body portion of the personal care device, the detachable portion comprising the cavity, the primary opening and the secondary opening.

2. The personal care device of claim 1, wherein the secondary opening is configured to further permit a flow of air via the secondary opening from the main body portion into the cavity and via the primary opening out of the cavity.

3. The personal care device of claim 2, wherein the secondary opening is configured such that, during use, the cavity is in fluidic communication with an internal air flow within the personal care device via the secondary opening.

4. The personal care device of claim 1, wherein the secondary opening is configured to be permanently open.

5. The personal care device of claim 1, wherein the secondary opening is provided along an axis:

tilting away from a direction of propagation of treatment energy generated by the energy source and incident upon the secondary opening during use; and/or passing through the primary opening of the cavity; and/or comprising a reflective surface configured to restrict a loss of treatment energy, generated by the energy source, from the cavity via the secondary opening.

6. The personal care device claim 1, wherein the cavity comprises at least one reflector wall configured to reflect and, thereby, direct treatment energy from the energy source towards the primary opening of the cavity, the secondary opening being provided in the reflector wall.

7. The personal care device of claim 1, wherein the secondary opening comprises a leading edge and a trailing edge, the leading edge being configured to extend beyond the trailing edge with respect to a direction of propagation of treatment energy incident upon the secondary opening, the secondary opening thereby being configured to restrict a loss of treatment energy from the cavity via the secondary opening.

8. The personal care device of claim 6, wherein the personal care device comprises:

an auxiliary reflector provided externally of the cavity and in alignment with the secondary opening, the auxiliary reflector being configured to reflect treatment energy propagating from the cavity into the secondary opening back into the cavity via the secondary opening; and/or a reflective surface provided within the secondary opening, the reflective surface being configured to restrict a loss of treatment energy from the cavity via the secondary opening.

9. The personal care device of claim 1, wherein the cavity comprises a plurality of secondary openings.

10. The personal care device of claim 1, further comprising a supporting surface surrounding the primary opening and arranged to contact and support the portion of the body during use, said supporting surface comprising at least one groove configured to be in fluidic communication with the cavity and with ambient air when the supporting surface is in contact with the portion of the body.

11. The personal care device of claim 1, further comprising a supporting surface surrounding the primary opening and arranged to contact and support the portion of the body during use, wherein at least one protrusion is provided on the supporting surface.

12. The personal care device of claim 1, wherein the personal care device is a skin care device.

13. The personal care device of claim 1, wherein the energy source comprises a light source and the treatment energy comprises intense pulsed light.

\* \* \* \* \*